United States Patent [19]
Inoue et al.

[11] 4,354,040
[45] Oct. 12, 1982

[54] PROCESS FOR SYNTHESIZING UREA

[75] Inventors: Shigeru Inoue, Kamakura; Hiroshi Ono, Fujisawa; Hidetsugu Fujii, Mobara, all of Japan

[73] Assignees: Toyo Engineering Corporation; Mitsui Toatsu Chemicals, Inc., both of Tokyo, Japan

[21] Appl. No.: 298,302

[22] Filed: Sep. 1, 1981

[30] Foreign Application Priority Data

Sep. 12, 1980 [JP] Japan .................. 55-126043

[51] Int. Cl.³ .................................. C07C 120/02
[52] U.S. Cl. ........................... 564/67; 564/70; 564/71; 564/72
[58] Field of Search ...................... 564/67, 71, 72

[56] References Cited
U.S. PATENT DOCUMENTS

| 3,090,811 | 5/1963 | Otsuka et al. ........... 564/67 |
| 3,711,544 | 1/1973 | Summerville et al. .... 564/71 |
| 4,081,469 | 3/1978 | Ono et al. .............. 564/67 |
| 4,110,374 | 8/1978 | Inoue .................... 564/71 |
| 4,301,299 | 11/1981 | Inoue et al. ............ 564/67 |

FOREIGN PATENT DOCUMENTS

| 1493038 | 1/1969 | Fed. Rep. of Germany ... 564/71 |
| 2654883 | 6/1977 | Fed. Rep. of Germany ... 564/72 |
| 46-16964 | 11/1971 | Japan ...................... 564/67 |

Primary Examiner—John Doll
Attorney, Agent, or Firm—Fisher, Christen & Sabol

[57] ABSTRACT

In a synthesis of urea using ammonia in a highly excessive molar ratio, unreacted materials are decomposed and separated by subjecting the urea synthesis effluent to a stripping step using carbon dioxide at a pressure equal to the urea synthesis pressure. The thus-separated gaseous mixture of ammonia and carbon dioxide is condensed through an indirect heat exchange with an effluent stream discharged from the stripping step and lowered to a predetermined pressure level. Resulting condensation heat is used for the decomposition and separation of unreacted materials still remaining in said effluent stream. By choosing suitable operation conditions for each step of the present invention, it is possible to reduce the amount of high pressure steam to be required and to minimize the amount of low pressure steam to be recovered.

4 Claims, 1 Drawing Figure

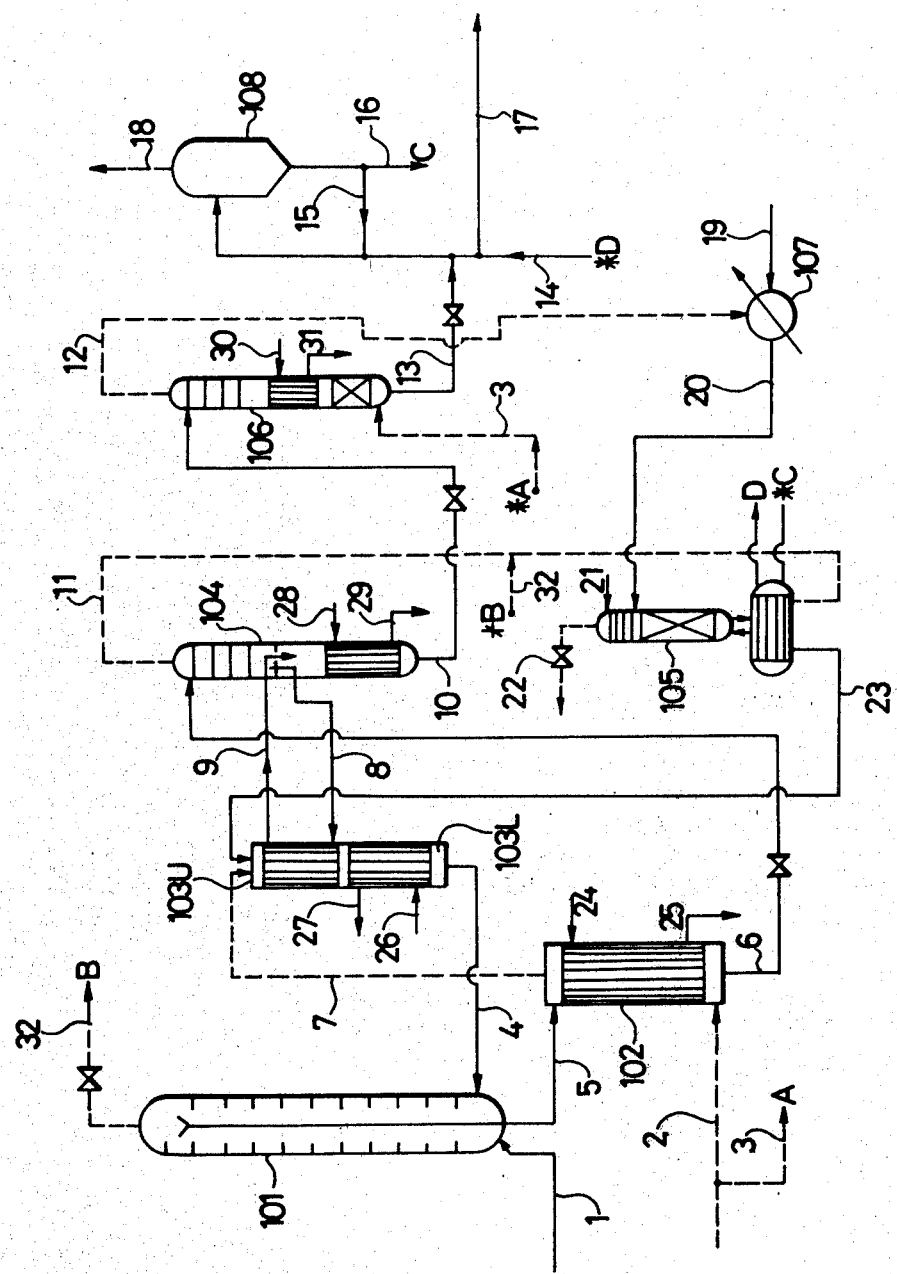

PROCESS FOR SYNTHESIZING UREA

BACKGROUND OF THE INVENTION (a) Field of the Invention

This invention relates to an improvement in the synthesis of urea. More particularly, it relates to a process for synthesizing urea with an improved thermal economy.

(b) Description of the Prior Art

With the recent steep rise in energy prices, it is now general practice to try to thoroughly recover thermal energy even in the production of urea. The thermal energy therein recovered is reutilized in the urea synthesis system and any extra thermal energy is estimated to be low pressure steam. According to the recent trend, the quantity of steam required for a urea synthesis process is determined by the difference between high pressure steam required in the reaction system for the decomposition and separation of unreacted ammonium carbamate and any excessive ammonia and the low pressure steam recovered (these ammonium carbamate and ammonia will hereinafter be referred to as "unreacted materials"). As the above-defined difference becomes smaller, a urea synthesis process is considered to be improved.

In the above sense, the so-called stripping process has been known as one of the outstanding urea synthesis processes. In the stripping process, urea synthesis effluent containing unreacted materials is subjected to a stripping step by carbon dioxide or ammonia, which is supplied as a raw material, at a pressure substantially equal to the urea synthesis pressure while being heated by high pressure steam of 25 kg/cm$^2$G, thereby to decompose and separate same from the resultant urea solution. A resultant gaseous mixture consisting of the thus-separated ammonia and carbon dioxide as well as the carbon dioxide or ammonia, which was used for the decomposition and separation of the unreacted materials, is then condensed under a pressure substantially equal to the stripping pressure. The condensation heat is recovered as low pressure steam of 2-5 kg/cm$^2$G. The resulting quantity of steam is so great that some steam would still remain even if consumed in steps capable of using such low pressure steam within the urea synthesis system, such as the condensation step. On the other hand, the urea synthesis effluent from which unreacted materials have been removed by stripping with carbon dioxide as described above is thereafter subjected to a low pressure decomposition under 1-5 kg/cm$^2$G and substantially all the remaining unreacted materials are decomposed in and separated from the urea synthesis effluent. The urea synthesis effluent from which unreacted materials have been removed through stripping by ammonia still contains a large quantity of ammonia therein. Thus, such urea synthesis effluent is first subjected to a high pressure decomposition under 10-25 kg/cm$^2$G and then to a low pressure decomposition under 1-5 kg/cm$^2$G. As heat sources for such high and low pressure decompositions, there are employed high pressure steam and low pressure steam. Generally speaking, the above-described stripping process is capable of recovering a considerable quantity of low pressure steam, but it requires a large quantity of high pressure steam for the following reasons. Namely, the stripping operation in the stripping process becomes easier to carry out as its pressure lowers. However, a urea synthesis effluent obtained by performing a urea synthesis at a relatively lower pressure contains a considerable amount of unreacted materials since the conversion ratio remains low at such a low pressure. Accordingly, it is necessary to use a large quantity of high pressure steam for the decomposition and separation of the unreacted materials.

To avoid the above-described difficulties, it becomes necessary to conduct a urea synthesis process at a higher urea synthesis pressure and temperature while maintaining ammonia in an excessive molar ratio with respect to carbon dioxide. This, however, creates another problem, namely, a higher urea synthesis pressure requires the stripping operation to be performed at a high pressure. It is, of course, possible to raise the operation temperature of the stripping operation with a view toward rendering the stripping operation easier. However, a stripping operation at high temperatures is accompanied by the drawback that more resultant urea is hydrolyzed.

SUMMARY OF THE INVENTION

An object of this invention is to provide an improved process for synthesizing urea through the use of ammonia in a highly excessive molar ratio, which process incorporates therein a stripping step using carbon dioxide.

Another object of this invention is to provide an improved process for synthesizing urea through the incorporation of a stripping step using carbon dioxide, which process features a lower demand for high pressure steam and a lower recovery rate of low pressure steam.

The present invention provides the following process for synthesizing urea: In a process for synthesizing urea including reacting in a urea synthesis zone ammonia and carbon dioxide at a urea synthesis pressure and temperature, separating from the resulting urea synthesis effluent unreacted materials as a gaseous mixture of ammonia and carbon dioxide, absorbing the gaseous mixture in an absorbent to form an absorbate, recycling the absorbate to the urea synthesis zone, and obtaining urea from an aqueous urea solution resulting from the separation step of the unreacted materials, the improvement which comprises:

(a) maintaining the temperature and pressure in the urea synthesis zone at 170°–195° C. and 160–190 kg/cm$^2$G, respectively and maintaining the molar ratio of whole ammonia/whole carbon dioxide to be charged into the urea synthesis zone within 3.5–5.0;

(b) subjecting the urea synthesis effluent from step (a) to a stripping step by carbon dioxide in an amount at least 60% of the make-up carbon dioxide and at a pressure equal to the urea synthesis pressure and a temperature in the range of 170°–205° C. to decompose the unreacted materials and separate same in the form of a gaseous mixture of ammonia and carbon dioxide, thereby lowering the total content of ammonia and carbon dioxide remaining in the urea synthesis effluent to 14–30% by weight;

(c) subjecting an effluent stream from step (b) to a high pressure decomposition under a pressure in the range of 12–25 kg/cm$^2$G to separate a part of the remaining ammonia and carbon dioxide by the condensation heat of the gaseous mixture separated in step (b), thereby lowering the total content of ammonia and carbon dioxide remaining in the effluent stream to 5–12% by weight;

(d) subjecting the effluent stream from step (c) successively to a low pressure decomposition, concentration and finishing steps;

(e) raising the pressure of an aqueous solution obtained by recovering ammonia and carbon dioxide separated in step (d), absorbing ammonia and carbon dioxide separated in step (c) in the thus-pressurized aqueous solution to form an absorbate, and using absorption heat generated upon absorbing ammonia and carbon dioxide as a heat source for the concentration step through an indirect heat exchange;

(f) raising the pressure of the absorbate obtained in step (e), condensing into the thus-pressurized absorbate the gaseous mixture separated in step (b) to form a condensate, and using a part of the condensation heat generated upon the condensation of the gaseous mixture for carrying out step (c) as defined in the above and removing a part of the remaining condensation heat by generating steam so as to maintain the urea synthesis temperature at a predetermined temperature; and (g) recycling the condensate and unabsorbed ammonia and carbon dioxide obtained in step (f) to the urea synthesis zone.

BRIEF DESCRIPTION OF THE DRAWING

The accompanying single drawing is a flow sheet included to explain one embodiment of this invention.

DETAILED DESCRIPTION OF THE INVENTION

Although the present invention may be applied to a conventional process for synthesizing urea through the use of ammonia in a slightly excessive molar ratio, it is suitable for applying the same to a urea synthesis process using the aforementioned high $NH_3/CO_2$ molar ratio. Generally speaking, a urea synthesis process using ammonia in a highly excessive molar ratio is a situation in which the molar ratio of whole ammonia to whole carbon dioxide to be supplied to a urea synthesis autoclave is at least 3.5, in many instances, 4 or higher. Here, a pressure of 200-250 kg/cm$^2$G and a temperature of 190°-200° C. are employed as urea synthesis conditions and the conversion ratio is as high as 65-72%. In order to decompose and separate unreacted materials contained in the urea synthesis effluent obtained under such conditions by a stripping operation at a pressure equal to the urea synthesis pressure, it is necessary to raise the temperature to at least 205° C. Moreover, since the above-described high conversion ratio results from the abundance of ammonia, urea is susceptible of being hydrolyzed when the majority of ammonia is removed at a temperature higher than the urea synthesis temperature.

The above-described various conditions have been chosen for the present invention by taking into integral consideration the ease of performing the stripping step, the condensation temperature of the gaseous mixture from the stripping step, utilization of the condensation heat to be generated for the decomposition under high pressure of unreacted materials remaining in the urea synthesis effluent from the stripping step, the absorption temperature of the gaseous mixture from the high pressure decomposition, and utilization of the absorption heat generated in the concentration step. More specifically, the $NH_3/CO_2$ molar ratio was set within 3.5-5.0. The urea synthesis pressure, stripping pressure and condensation pressure of the gaseous mixture from the stripping step were each set within 160-190 kg/cm$^2$G. Below 160 kg/cm$^2$G, neither the desired high conversion ratio nor the desired high condensation of the gaseous mixture can be reached. On the other hand, beyond 190 kg/cm$^2$G, it is necessary to raise the stripping temperature.

As the stripping temperature, a temperature range of 170°-205° C. was chosen. Below 170° C., the unreacted materials would not be separated to an intended degree, whereas, above 205° C., a drawback arises in that the hydrolysis of urea is accelerated as mentioned above. The total content of ammonia and carbon dioxide remaining in the urea synthesis effluent from the stripping step was set within 14-30% by weight. Although it is more preferable to lower the aforementioned total content below the lower limit, this requires an increase in the stripping temperature which increase raises the above-described problem of hydrolysis of urea. On the other hand, when the aforementioned total content exceeds its upper limit, the absorption heat of the gaseous mixture from the decomposition under high pressure becomes much greater than that required for the concentration step and, thus, more cooling water is required.

The urea synthesis effluent from the stripping step is subjected to a high pressure decomposition under 12-25 kg/cm$^2$G. Under the lower limit, the absorption temperature of the gaseous mixture from the high pressure decomposition cannot be raised to 80° C. or higher and the resulting absorption heat cannot be used for the concentration step. In addition, it would become difficult to condense the unabsorbed, excessive ammonia contained in the gaseous mixture with cooling water. On the other hand, beyond the upper limit, it becomes necessary to raise the temperature of the high pressure decomposition step further. This may result in the equalization of the temperature of the high pressure decomposition step with the condensation temperature of the gaseous mixture from the stripping step, or on the contrary, it may render the former temperature higher than the latter temperature, thereby making it impossible to directly use the condensation heat of the gaseous mixture from the stripping step as a heat source for the high pressure decomposition step. It is necessary to make the temperature of the high pressure decomposition step lower, at least during a stage of the decomposition step, than the condensation temperature of the gaseous mixture from the stripping step. This temperature difference is preferably at least 5° C. and is determined so as to decompose and separate by the aforementioned condensation heat preferably at least 30% by weight of the unreacted materials contained in the urea synthesis effluent fed into the high pressure decomposition step. In the high pressure decomposition step, the urea synthesis effluent may be heated to 160°-175° C. by heating same with steam. The total content of ammonia and carbon dioxide remaining in the urea solution discharged from the high pressure decomposition step is in the range of 5-12% by weight. If the temperature to be reached by steam heating is too low or the unreacted materials remaining in the urea solution are too much, insufficient absorption heat is liberated upon the absorption of the gaseous mixture from the high pressure decomposition and the heat required for the concentration step cannot be provided satisfactorily. On the other hand, if the temperature exceeds the above-described upper limit, the problem of hydrolysis of urea arises again.

The condensation temperature of the gaseous mixture from the stripping step must be higher, preferably by at least 5° C., than the temperature of the high pressure decomposition step at least during a stage of the condensation step. For example, if the condensation temperature is 155° C., the temperature of the high pressure decomposition step should not be higher than 150° C., at least during a stage of the decomposition step.

The amount of carbon dioxide employed for the stripping step should be at least 60% of that charged as a raw material since the urea synthesis is carried out using an excessive amount of ammonia.

According to the present invention, various conditions of the varied steps are skillfully combined together to enable the synthesis of urea with a lesser consumption of high pressure steam and a lesser recovery of low pressure steam. Among numerous effects derived from this invention, there are mentioned specifically the following ones:

(1) The stripping operation by carbon dioxide has been effectively incorporated in a urea synthesis process using ammonia in a highly excessive molar ratio although such an incorporation has heretofore been considered difficult;

(2) In a urea synthesis process incorporating the conventional stripping step, the consumption of high pressure steam and recovery of low pressure steam are both high (although a process is considered to be more efficient as the difference between both of the above-mentioned steams becomes smaller). This invention has reduced the amount of high pressure steam required for the high pressure decomposition as described above (in other words, the recovery of low pressure steam has also been reduced in quantity), thereby solving the drawback of a urea synthesis process using the conventional stripping step that consumes in great quantity high pressure steam of a high value and recovers also in great quantity low pressure steam of a low value.

(3) The construction cost of production facilities can be lowered. More specifically, a part of the condenser for the gaseous mixture from the stripping step is employed also as a heater for the high pressure decomposition step. Therefore, a heater for the high pressure decomposition has been made in part unnecessary.

It is also possible in the present invention to make the pressure in the high pressure decomposition step lower than the absorption pressure of the gaseous mixture from the high pressure decomposition step and to raise the pressure of the gaseous mixture from the decomposition step to the same as the absorption pressure prior to carrying out the absorption. This facilitates the use of the condensation heat of the gaseous mixture from the stripping step as a heat source for the high pressure decomposition because it is possible to make the temperature of the high pressure decomposition step still lower. Furthermore, since any high pressure convenient for the absorption of the gaseous mixture from the high pressure decomposition step may be chosen freely independent from the pressure of the high pressure decomposition step, it is possible to raise the absorption temperature. This is certainly advantageous for the utilization of the resultant absorption heat.

Now, an embodiment for practicing this invention is described hereinbelow in accordance with the accompanying single drawing.

EXAMPLE

A urea synthesis autoclave 101 was charged with 568 kg/hr of liquefied ammonia through a line 1 as well as 1267 kg/hr of ammonia, 1129 kg/hr of carbon dioxide and 265 kg/hr of water in a gas-liquid mixed phase at 165° C. through a line 4. The synthesis autoclave 101 was operated at 185 kg/cm$^2$G and 192° C., with a residence time of about 1 hour. A urea synthesis effluent was obtained through a line 5 with a conversion ratio of 69%, in other words, a urea synthesis effluent containing 1042 kg/hr of urea, 1118 kg/hr of ammonia, 340 kg/hr of carbon dioxide and 570 kg/hr of water was obtained. On the other hand, from the top of the synthesis autoclave 101, a gaseous mixture containing inert gases (127 kg/hr of ammonia, 25 kg/hr of carbon dioxide and 7 kg/hr of water) was discharged and fed through a line 32 to a lower portion of a high pressure absorption column 105. The thus-obtained urea synthesis effluent was led through a line 5 to the top of a stripper 102 which was operated at the same pressure as the urea synthesis autoclave 101. While flowing down along a falling film heater disposed in the stripper 102, unreacted materials were separated from the effluent by stripping them off through the heating by high pressure steam of 25 kg/cm$^2$G from a line 24 and by means of pressurized carbon dioxide (160° C.) charged through a line 2 at a flow rate of 676 kg/hr. From the bottom of the stripping column 102, was drawn out through a line 6 and at 198° C. a solution consisting of 1019 kg/hr of urea, 205 kg/hr of ammonia, 201 kg/hr of carbon dioxide and 494 kg/hr of water.

The solution was immediately flashed under a reduced pressure of 18 kg/cm$^2$G and then introduced into a high pressure decomposition column 104. The flashing took place at 145° C. The high pressure decomposition column 104 was formed of a rectification zone having sieve trays arranged in several stages and a heater provided below the sieve trays and having high pressure steam inlet and outlet lines 28 and 29. The solution at 155° C. on the sieve tray in the lowermost stage was fed through a line 8 to the shell side in an upper part 103U of a carbamate condenser, which will be described hereinlater, where the solution was heated and returned to the high pressure decomposition column 104 through a line 9 while liberating a part of unreacted materials.

The gaseous mixture of ammonia and carbon dioxide separated in the high pressure decomposition column 104 ascended through the sieve trays together with a gaseous mixture of ammonia and carbon dioxide which had come up from the heater. On the other hand, the solution was heated to 162° C. and further heated at the heater by means of the high pressure steam from line 28, thereby reducing in quantity the unreacted materials to a predetermined level. The solution after the removal of unreacted materials consisted of 1008 kg/hr or urea, 100 kg/hr of ammonia, 33 kg/hr of carbon dioxide and 460 kg/hr of water. This solution was led through a line 10 to a low pressure decomposition column 106 and then through a line 13 to a vacuum concentrator 108 where the decomposition of unreacted materials and the concentration of the solution were respectively carried out. To the low pressure decomposition column 106, 58 kg/hr of carbon dioxide was introduced as a stripping gas through the line 3. On the other hand, the gaseous mixture separated from the high pressure decomposition column 104 was led to a lower part of the high pressure absorption column 105 at 17.5 kg/cm²G together with the purged gas supplied through the line 32 from the synthesis autoclave 101. In the lower part of the high pressure absorption column 105, the gaseous mixture was absorbed at 100° C. The absorption heat generated was removed by means of a urea slurry, which has a temperature of 65° C. and contains urea crystals, supplied through a line 16 from the vacuum concentrator 108. The thus-heated urea slurry was returned through a line 14 to the vacuum concentrator 108. Of the thus-heated urea slurry, a portion equivalent to yield the final product, urea, in an amount of 1124 kg/hr was delivered to a finishing step through a line 17 while the remainder was recycled to the vacuum concentrator 108 to cause a desired amount of water to evaporate.

A slight amount of gases unabsorbed in the lower part of the high pressure absorption column 105 was absorbed by the aqueous solution containing ammonia and carbon dioxide (ammonia: 103 kg/hr, carbon dioxide: 96 kg/hr, and water: 148 kg/hr) introduced through a line 20 from the low pressure absorber 107 and water charged at a flow rate of 15 kg/hr through a line 21 while ascending through the packed portion in the high pressure absorption column 105 and flowed down into the lower part thereof. From the top of the high pressure absorption column 105, practically inert gases only were purged through a line 22. From the cooler installed at the lower part of the high pressure absorption column 105, was obtained a solution consisting of 341 kg/hr of ammonia, 297 kg/hr of carbon dioxide and 196 kg/hr of water.

The solution was then pressurized to 185 kg/cm²G and supplied through a line 23 to the heat exchange part at the upper portion 103U of a carbamate condenser. Here, a part of the gaseous mixture (ammonia: 926 kg/hr, carbon dioxide: 832 kg/hr, and water 69 kg/hr) of 195° C. from stripper 102 was condensed and absorbed in the solution. The resulting heat was, as mentioned above, removed by the urea solution supplied through line 8 from high pressure decomposition column 104. The thus-removed heat was equivalent to 150 kg/hr of steam. The absorption temperature reached 168° C. The gaseous mixture unabsorbed in the upper part 103U of the carbamate condenser was led to the heat exchanger at the lower part 103L of the carbamate condenser, where a part of the unabsorbed gaseous mixture absorbed in such an amount that enables to obtain in the synthesis autoclave 101 a urea synthesis effluent of a predetermined temperature. The heat generated through the absorption was recovered as low pressure steam of 4 kg/cm²G. After the absorption, the temperature of the absorption solution reached 165° C. as mentioned above and was recycled to the synthesis autoclave 101 together with the remaining part of the unabsorbed gaseous mixture in the form of a gas-liquid mixed phase. Low pressure steam was recovered in an amount of 530 kg/hr, of which 400 kg/hr was used for the low pressure decomposition column 106 and the finishing step, for recovering slight amounts of ammonia and carbon dioxide contained in the evaporated water obtained through a line 18 from the vacuum concentrator 108, etc. while the remaining 130 kg/hr was taken out of the urea synthesis system as surplus. As a result, since high pressure steam was used in an amount of 670 kg/hr principally for the stripper and high pressure decomposition, 540 kg/hr of steam was consumed in the present urea synthesis process. If no heat exchange were performed in the carbamate condenser and high pressure decomposition column while maintaining the other operation conditions as same as the above-mentioned process, the high pressure steam would be consumed in the amount of 670+150=820 kg/hr and the surplus low pressure would be recovered in the amount of 130+150=280 kg/hr.

What is claimed is:

1. In a process for synthesizing urea including reacting in a urea synthesis zone ammonia and carbon dioxide at a urea synthesis pressure and temperature, separating from the resulting urea synthesis effluent unreacted materials as a gaseous mixture of ammonia and carbon dioxide, and absorbing the gaseous mixture in an absorbent to form an absorbate, recycling the absorbate together with the gaseous mixture to the urea synthesis zone, and obtaining urea from an aqueous urea solution resulting from the separation step of the unreacted materials, the improvement which comprises:

(a) maintaining the temperature and pressure in the urea synthesis zone at 170°–195° C. and 160–190 kg/cm²G and maintaining the molar ratio of whole ammonia/whole carbon dioxide to be charged into the urea synthesis zone within 3.5–5.0;

(b) subjecting the urea synthesis effluent from step (a) to a stripping step by carbon dioxide in an amount at least 60% of the make-up carbon dioxide and at a pressure equal to the urea synthesis pressure and a temperature in the range of 170°–205° C. to decompose the unreacted materials and separate the same in the form of a gaseous mixture of ammonia and carbon dioxide, thereby lowering the total content of ammonia and carbon dioxide remaining in the urea synthesis effluent to 14–30% by weight;

(c) subjecting an effluent stream from step (b) to a high pressure decomposition under a pressure in the range of 12–25 kg/cm²G to separate a part of the remaining ammonia and carbon dioxide by the condensation heat of the gaseous mixture separated in step (b), thereby lowering the total content of ammonia and carbon dioxide remaining in the effluent stream to 5–12% by weight;

(d) subjecting the effluent stream from step (c) successively to a low pressure decomposition, concentration and finishing steps;

(e) raising the pressure of an aqueous solution obtained by recovering ammonia and carbon dioxide separated in step (d), absorbing ammonia and carbon dioxide separated in step (c) in the thus-pressurized aqueous solution to form an absorbate and using absorption heat generated upon absorbing ammonia and carbon dioxide as a heat source for the concentration step through an indirect heat exchange;

(f) raising the pressure of the absorbate obtained in step (3) condensing into the thus-pressurized absorbate the gaseous mixture separated in step (b) to form a condensate, and using a part of the condensation heat generated upon the condensation of the gaseous mixture for carrying out step (c) as defined in the above and removing a part of the remaining condensation heat by generating steam so as to maintain the urea synthesis temperature at a predetermined temperature; and (g) recycling the condensate and unabsorbed ammonia and carbon dioxide obtained in step (f) to the urea synthesis zone.

2. The process as claimed in claim 1, wherein, in step (f), the condensation temperature is higher by at least 5° C. than the high pressure decomposition temperature in step (c) at least during a stage of the condensation step.

3. The process as claimed in claim 1, wherein, in step (e), the absorption is carried out at a temperature not lower than 80° C.

4. The process as claimed in claim 1, wherein, in step (c), the effluent stream from step (b) is subjected to a high pressure decomposition under a pressure of from 12 to 25 kg/cm$^2$G to separate at least 30% by weight by the condensation heat of the gaseous mixture separated in step (b), and thereafter the resulting effluent stream is heated to 160°–175° C. by steam to further lower the total content of ammonia and carbon dioxide remaining in the effluent stream to 5–12% by weight.

* * * * *

REEXAMINATION CERTIFICATE (902nd)

United States Patent [19]

Inoue et al.

[11] B1 4,354,040
[45] Certificate Issued  Jul. 26, 1988

[54] PROCESS FOR SYNTHESIZING UREA

[75] Inventors: Shigeru Inoue, Kamakura; Hiroshi Ono, Fujisawa; Hidetsugu Fujii, Mobara, all of Japan

[73] Assignees: Toyo Engineering Corporation; Mitsui Toatsu Chemicals, Inc., both of Tokyo, Japan Reexamination Request:
No. 90/000,850, Sep. 3, 1985

Reexamination Certificate for:
Patent No.: 4,354,040
Issued: Oct. 12, 1982
Appl. No.: 298,302
Filed: Sep. 1, 1981

Disclaimer of Claim
(s) 1-4 Filed: Feb. 3, 1988 (1090 O.G. 63)

[30] Foreign Application Priority Data

Sep. 12, 1980 [JP] Japan ............... 55-126043

[51] Int. Cl.⁴ ............................... C07C 126/02
[52] U.S. Cl. ........................... 564/67; 564/70; 564/71; 564/72
[58] Field of Search ............... 564/67, 70–72

[56] References Cited

U.S. PATENT DOCUMENTS

| | | | |
|---|---|---|---|
| 3,090,811 | 5/1963 | Otsuka et al. | 260/555 |
| 3,137,725 | 6/1964 | Cook et al. | 260/555 |
| 3,281,464 | 10/1966 | Tsao . | |
| 3,356,723 | 12/1967 | Kaasenbrood . | |
| 3,668,250 | 6/1972 | Karafian . | |
| 3,686,305 | 8/1972 | Otsuka et al. . | |
| 3,886,210 | 5/1975 | Mavrovic | 260/555 A |
| 3,936,500 | 2/1976 | Kaasenbrook et al. | 260/555 A |
| 3,957,868 | 5/1976 | Verstegen et al. . | |
| 4,154,760 | 5/1979 | Otsuka et al. | 260/555 A |
| 4,231,961 | 11/1980 | Konoki et al. | 564/65 |
| 4,334,096 | 6/1982 | Konoki et al. | 564/72 |

FOREIGN PATENT DOCUMENTS

| | | | |
|---|---|---|---|
| 46-16963 | of 0000 | Japan . | |
| 0000089 | 1/1976 | Japan | 564/70 |
| 8000343 | 3/1980 | Japan . | |
| 2040283 | 8/1980 | United Kingdom . | |

OTHER PUBLICATIONS

Perry & Chilton, Chemical Engineers' Handbook, McGraw-Hill, 5th Ed. (1973), pp. 18-3 to 18-5.
McCabe & Smith, Unit Operations of Chemical Engineering, McGraw-Hill (1956), pp. 683-686.
Kirk-Othmer, Encyclopedia of Chemical Technology, (Wiley 1970), vol. 21, pp. 49-50.

Primary Examiner—Charles F. Warren

[57] ABSTRACT

In a synthesis of urea using ammonia in a highly excessive molar ratio, unreacted materials are decomposed and separated by subjecting the urea synthesis effluent to a stripping step using carbon dioxide at a pressure equal to the urea synthesis pressure. The thus-separated gaseous mixture of ammonia and carbon dioxide is condensed through an indirect heat exchange with an effluent stream discharged from the stripping step and lowered to a predetermined pressure level. Resulting condensation heat is used for the decomposition and separation of unreacted materials still remaining in said effluent stream. By choosing suitable operation conditions for each step of the present invention, it is possible to reduce the amount of high pressure steam to be required and to minimize the amount of low pressure steam to be recovered.

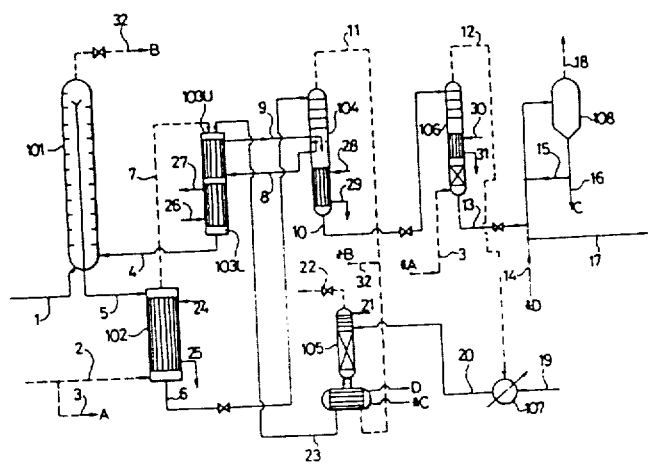

REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1–4 are now disclaimed.

* * * * *